United States Patent
Wenner et al.

(10) Patent No.: US 6,440,061 B1
(45) Date of Patent: Aug. 27, 2002

(54) LAPAROSCOPIC INSTRUMENT SYSTEM FOR REAL-TIME BILIARY EXPLORATION AND STONE REMOVAL

(76) Inventors: Donald E. Wenner, 3600 Kessler Pl.; George L. Scott, III, 3103 Diamond A, both of Roswell, NM (US) 88201

( * ) Notice: Subject to any disclaimer, the term of this patent is extended or adjusted under 35 U.S.C. 154(b) by 0 days.

(21) Appl. No.: 09/534,789

(22) Filed: Mar. 24, 2000

(51) Int. Cl.[7] .................................................. A61B 1/04
(52) U.S. Cl. ...................... 600/114; 600/115; 604/43; 604/264; 606/108
(58) Field of Search ................................. 600/114, 115; 604/27, 43, 264, 277; 606/108

(56) References Cited

U.S. PATENT DOCUMENTS

| | | | | |
|---|---|---|---|---|
| 5,209,741 A | * | 5/1993 | Spaeth | 604/264 |
| 5,374,273 A | | 12/1994 | Nakao et al. | |
| 5,380,277 A | * | 1/1995 | Phillips | 604/33 |
| 5,470,320 A | * | 11/1995 | Tiefenbrun et al. | 604/174 |
| 5,695,448 A | * | 12/1997 | Kimura et al. | 600/121 |
| 5,792,044 A | * | 8/1998 | Foley et al. | 600/114 |
| 5,891,013 A | * | 4/1999 | Thompson | 600/104 |

* cited by examiner

*Primary Examiner*—Linda C. M. Dvorak
*Assistant Examiner*—Jocelyn Ram
(74) *Attorney, Agent, or Firm*—Loren G. Helmreich; Browning Bushman, PC

(57) ABSTRACT

A laparoscopic port adapter assembly 10 for conducting bile duct and related procedures, including a laparoscopic port 11, an introducer sheath 12 and a multiple conduit instrument guide 13. The instrument guide 13 may be inserted into a bile duct 14 to facilitate concurrent introduction of multiple instruments directly into the bile duct 14 without need for forceps manipulation of instruments through additional laparoscopic ports. The procedure may be conducted and viewed in real-time video to improve procedural efficiency and safety. Inventive related useful instruments and procedures are included to complement use and flexibility of the laparoscopic port adapter assembly 10. A preferred embodiment may include use of a three-conduit instrument guide 13 and concurrent introduction of a lithotripter 32, choledochoscope 31 and irrigative catheter 34 directly in the bile duct 14.

33 Claims, 6 Drawing Sheets

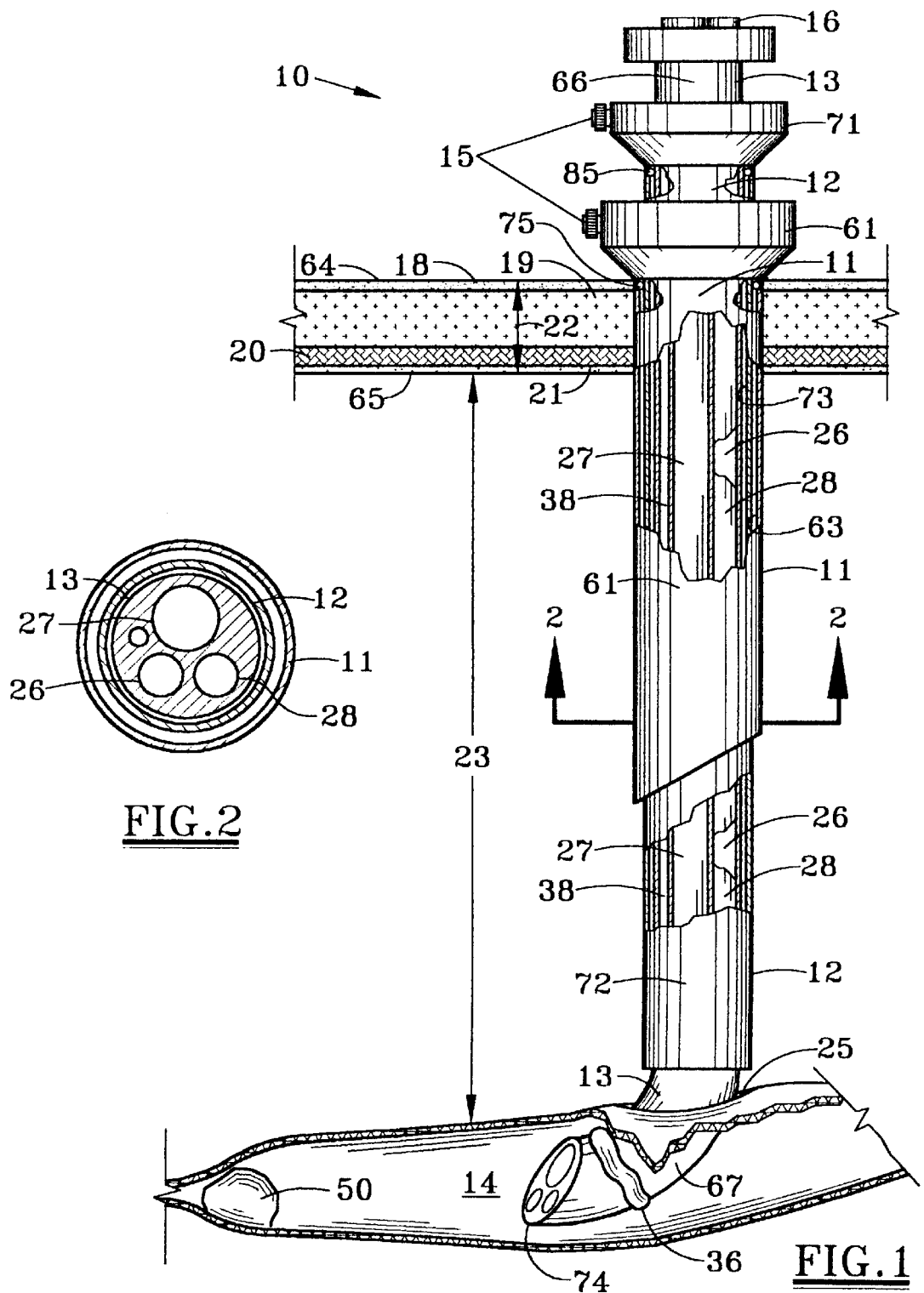

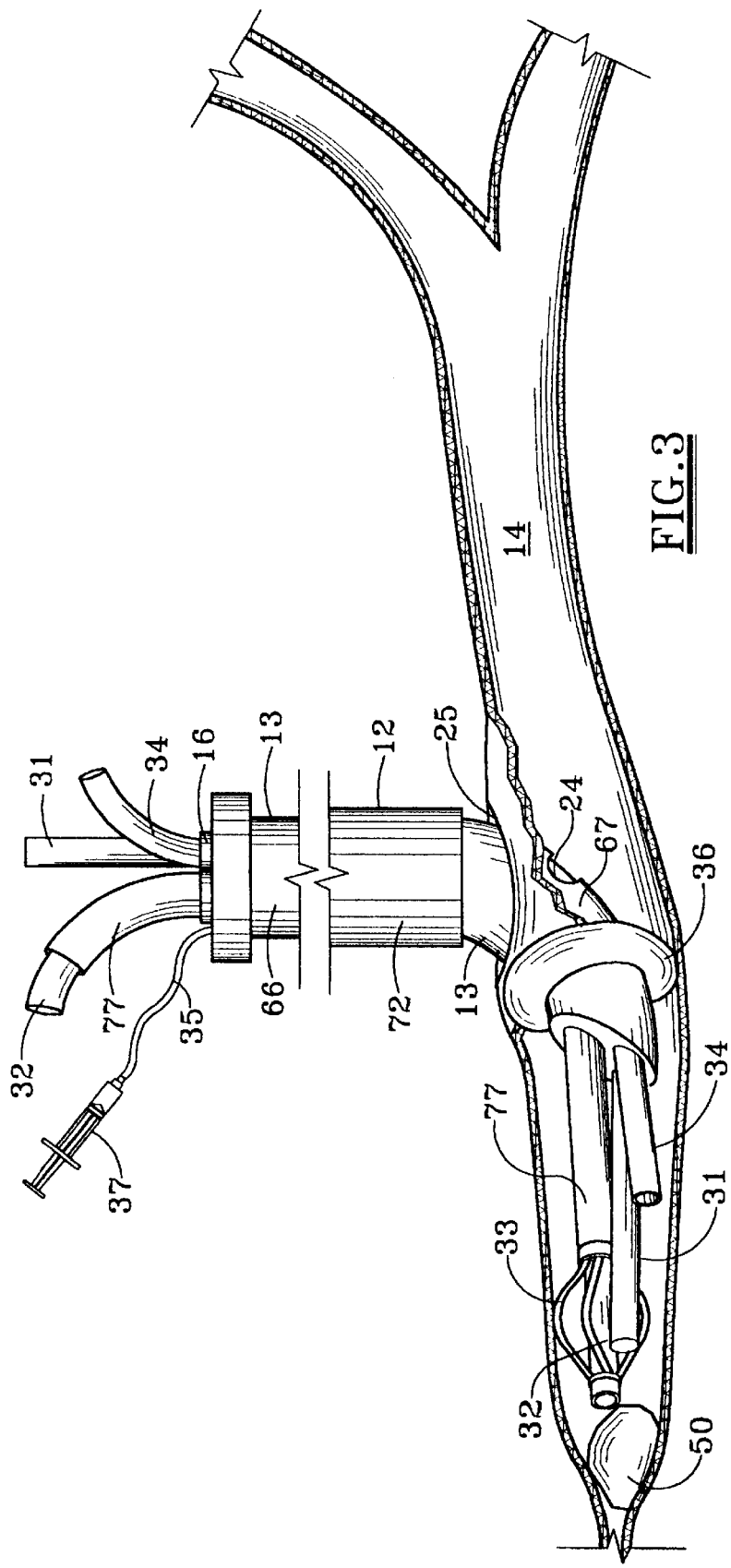

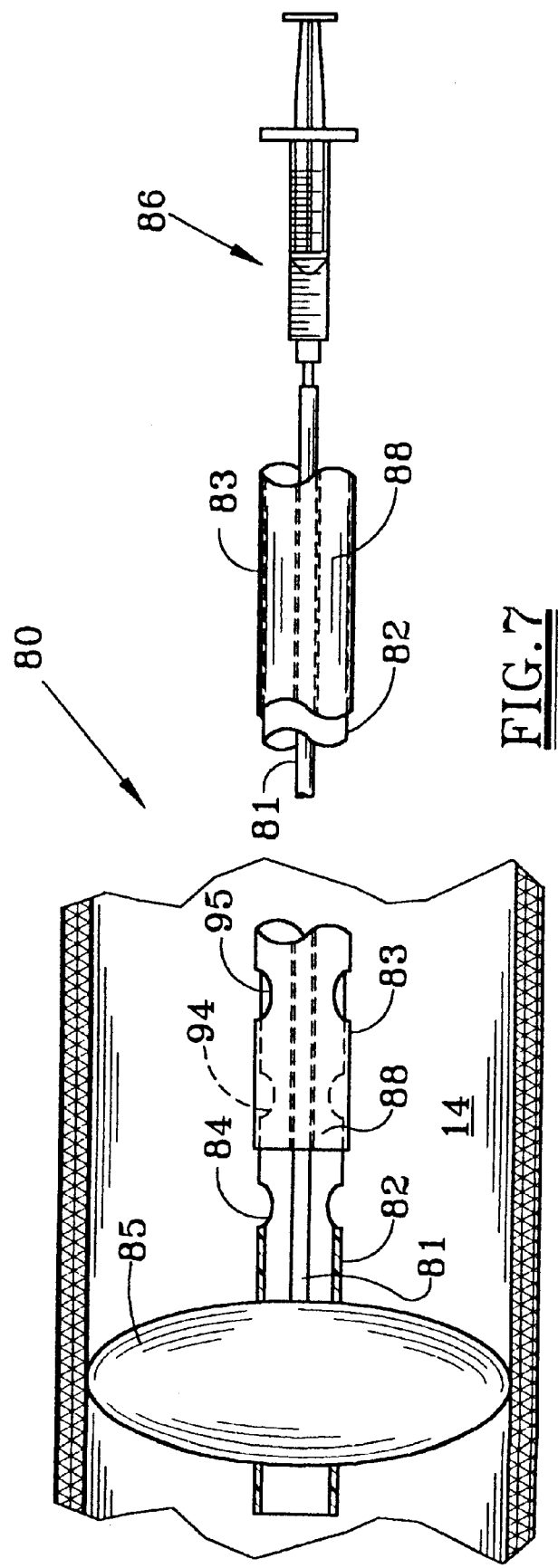

LAPAROSCOPIC INSTRUMENT SYSTEM FOR REAL-TIME BILIARY EXPLORATION AND STONE REMOVAL

FIELD OF THE INVENTION

The present invention relates generally to medical equipment and more particularly to laparoscopic surgical instruments of the type used in biliary tract procedures. The surgical instruments described herein facilitate common bile duct exploration and the removal of physiologic calculi, generally referred to as stones. The invention provides enhancements related to systematic insertion, deployment and manipulation of various instruments including a choledochoscope for concurrent real-time viewing of the laparoscopic surgical process.

BACKGROUND OF THE INVENTION

Many patients develop stones within their gall bladder, which may pass through the cystic duct to become lodged in the common bile duct, a condition known as choledocholithiasis. Stones are typically variable in size from 1.00–20.00 mm. These stones may block the common bile duct, the hepatic duct or intrahepatic ducts, and if untreated may result in obstructive jaundice that may result in cholangitis (infection within the biliary tract) and severe discomfort to the patient, or death due to sepsis or liver dysfunction. Solitary or multiple stones may be loose within the common bile duct or otherwise embedded into the common bile duct wall, or impacted at the Papilla of Vater. This condition typically requires concurrent surgical removal of the gall bladder along with removal of the stones from the common bile duct. This surgical procedure is referred to as cholecystectomy with common bile duct exploration.

The presence of stones in a patient's biliary tract is confirmed using typical diagnostic methods, such as cystic duct cholangiography or ultrasonography. Stones are also often discovered during laparoscopic cholecystectomy, a procedure for removal of the gall bladder. Common bile duct stones may also be anticipated preoperatively due to physical symptoms including jaundice, or from blood tests that indicates liver function abnormality. This condition is typically confirmed intraoperatively during cholecystectomy with cholangiography or by ultrasound.

Stone removal is conventionally attempted by various invasive surgical procedures for common bile duct exploration and stone removal, including; 1) open common bile duct exploration, 2) an endoscopic surgery known as endoscopic retrograde cholangio-pancreatography (ERCP), and 3) laparoscopic common bile duct exploration. Open surgery typically requires a substantially more invasive surgical incision with associated pain, increased length of hospitalization and prolonged recovery period, as compared to typical laparoscopic procedures.

Alternately, the ERCP procedure is limited to only the most skilled endoscopist. An additional specialist is required to perform this procedure. ERCP may not be effective and often further delays definitive treatment of the condition. ERCP is also associated with an increased risk of harm and even death due to pancreatitis.

Laparoscopic common bile duct exploration is typically the most desirable procedure for stone removal. This method of stone removal is often difficult and tenuous in performance due to various limitations in instrumentation, and as a result of the unique difficulties encountered by the surgeon in each operative procedure.

An array of laparoscopic surgical instruments are used for common bile duct exploration and stone retrieval, including balloon catheters, irrigation catheters, stone baskets, biopsy forceps, papillatome (to cut the Papillae of Vater), and lithotripter or fiber laser (to pulverize the calculi). These instruments and fiber-optic choledochoscope for viewing are passed through laparoscopic ports during the surgical procedure. Grasping forceps, which are inserted into the abdominal region via separate port incisions, are simultaneously deployed to position the various tools and choledochoscope.

Choledochoscopes include an array of fiber optic channels for light and image transmission, and a cable system that allows the surgeon to maneuver the distal tip of the instrument for viewing purposes. Choledochoscopes typically include a working channel for irrigation fluid or for deployment of various instruments such as basket, balloon or lithotripter instruments. These instruments are size-restricted (less than 3.0 mm) as a function of the working channel's relatively small diameter. Visualization within the bile duct is impaired as a result of restricted fluid flow when the working channel is occupied by a tool, and as a result of ineffective hydraulic distension of the bile duct. Said visual impairment results from an obstructive murk comprised of bile, blood and stone debris. A larger diameter (4–8 mm) choledochoscopes may be used to overcome the aforementioned limitations via the advantage of a larger working channel. The larger choledochoscopes are less fragile in comparison to the smaller diameter choledochoscopes, which are easily damaged by manipulation with grasping forceps. However, there is a disadvantage to using larger diameter scopes as they typically will not traverse the smaller regions of the biliary tree, or the papillae of Vader. In addition, many patients are characterized by common bile ducts of a relatively small diameter, thus precluding use of the larger diameter choledochoscopes.

Generally only one surgical instrument is deployed at a time into the common bile duct, or otherwise said instrument may be run combined in a tandem arrangement with the choledochoscope. Said tandem array typically also includes either an open working channel or other instrument, which is longitudinally attached. This tandem combination allows insertion of a single instrument tool via the working channel for deployment within the common bile duct. Use of said working channel may be problematic, however, if the required flow of irrigating fluid through the working channel is impaired by simultaneous deployment of an instrument through that same channel.

The terms "upper" and "lower" may be used herein to describe opposite ends of various components, or a relative position of various components. A component may include an "upper" end, which denotes the end that is axially oriented away from penetration of the patient, and "lower" denotes an end that is oriented toward penetration of the patient. Biliary and cystic duct exploration and related calculus removal procedures typically include a strategically distributed set of four or five ports. Each port may be generally positioned such that the lower ends are oriented toward a common focus or apex in the vicinity of the biliary tract. Various tubular instrument guides and laparoscopic surgical instruments may be inserted through these ports to accomplish the cholecystectomy and operative cholangiogram procedure, including dissecting forceps, scissors, grasping forceps, stone forceps, cholangiogram catheter, and cautery instruments. The cylindrical, tubular laparoscopic ports are typically 5–12 mm ID and of length adequate to penetrate through the abdominal wall to the area adjacent to the common bile duct, which is referred to as the porta hepatis. Laparoscopic ports also have valve mechanisms that prevent the loss of pneumoperitoneum, which is the gas pressure (typically under 12–15 cm H2O pressure) introduced into the peritoneal cavity to provide working space for instrument manipulation and to facilitate visualization of anatomic structures within the peritoneal cavity. Carbon dioxide is the gas employed most commonly to establish this insufflation of the patient's abdominal cavity during laparoscopic surgical procedures. The port optionally provides for the introduction of a tubular sheath through the port to extend the instrument access conduit deeper into the abdominal cavity. Both the port and introducer sheath may each provide inner and outer annular seals, with valves by which to sustain and regulate abdominal sufflation. The upper end of the laparoscopic port may contain a valve and a fitting for attachment to a CO2 source to control insufflation and desufflation. The port and the sheath may be fabricated from metallic or resinous material, including, for example, stainless steel, plastic, nylon or polyethylene.

The sheath, in varying embodiments, may also be referred to as a rigid introducer sheath or guide sleeve. This introducer sheath, typically having an OD in the range of five to nine millimeters, may extend along the entire axial length of the port, extending above the upper opening of the port and to below the lower end of the port. Sheath depth is typically adjustable and may be affixed to a desired depth of penetration. The sheath may function as a carrier for a surgical instrument or combined tools via a single conduit in the tube. The introducer sheath thus provides access through which to selectively insert, manipulate and retrieve tools and instruments useful in various laparoscopic procedures including those involving the gall bladder and biliary tract. The most common introducer sheath is a mono-bore design with a heavy wall, which may be either, a straight bore variety or a type that includes a curved or bent tip. A disadvantage of the mono-bore, heavy walled design is that the cross-sectional diameter of the conduit that may be used for inserting instruments in tandem is very limited, especially while a choledochoscope is concurrently inserted. Thus, the diameter size of working channel requires a selection of instruments that are relatively small. In addition, the larger diameter instruments may have to be utilized singularly in a port or in alternating succession, thus requiring removal of the choledochoscope prior to instrument use. Removal of stones or debris may also be limited by the small diameter of the conduit. Other prior art introducer sheaths for laparoscopic surgery may include a substantially straight bore, as opposed to those introducers providing a curved or bent lower end. This style introducer sheath presents handicaps as precise placement and orientation of the multiple-ports, guide tubes, scope, and/or instrument array is made more critical, complex and difficult to maneuver, and frequently requires use of forceps which may add to the risk of damage to the fragile choledochoscope. For either, the straight bore or bent-end variety of introducer sheath, under prior art, the range of extension and angular deflection may be limited. Precise placement of instruments and/or the choledochoscope, such as through the incision in the common bile duct and then maneuvering through the duct may be very difficult, necessitating use of forceps from other orientations to assist in maneuvering. In addition, the farther a flexible scope or instrument is extended beyond the introducer the more difficult if may be to manipulate or direct that device through the incision into the common bile duct or around obstructions and through the tortuous passageways of the biliary tree.

Following insertion of the array of ports and upon confirmation of choledocholithiasis (presence of bile duct stones), a procedure is required to retrieve the stones. This may be attempted by either a transcystic duct retrieval or via a longitudinal incision in the common bile duct, referred to as a choledochotomy. Various known laparoscopic instruments are introduced into the bile duct to attempt removal or destruction of stones, and subsequent procedures are often required if the initial attempts are unsuccessful, including irrigating to remove the stones, basket extraction, or shockwave lithotripsy to destroy stones in situ. Each penetration with an instrument through a port is typically preceded by and followed by a choledochoscopic examination to view progress, and to diagnose or modify the procedure as necessary.

The surgeon typically attempts to extract stones from the common bile duct by various methods and by use of different instruments. Stones may be removed by circulating with irrigating fluids, by extraction with forceps, balloon catheter or stone basket, or by use of electrohydraulic lithotripter or fiber laser. Alternately the surgeon may displace stones through the papilla of Vader. After each attempt, a choledochoscope is typically inserted to inspect the common bile duct and assess the efficacy of stone retrieval to allow subsequent corrections as needed in the positioning of instruments thereof. For maneuvering and manipulation of the choledochoscope within the bile duct, forceps are commonly used to grasp, guide and control insertion. Unfortunately, choledochoscopes are relatively fragile and easily damaged. The procedure to remove common bile duct stones typically involves a series of insertions and extractions through the array of laparoscopic ports. One such array may include ports located in the right upper abdominal quad and right lower abdominal quad for grasping forceps, an umbilical port for the laparoscope, and an epigastric port for other instruments. Other ports and instrument variations are possible. Precise placement of instruments and the choledochoscope into the choledochotomy (the incision in the common bile duct) and subsequent maneuvering through the duct may be very difficult, necessitating use of forceps from other orientations to assist in maneuvering. In addition, the farther a flexible scope, cannula or instrument is extended beyond the introducer, the more difficult if may be to manipulate or direct that device through an incision into the common bile duct or around obstructions and through the tortuous passageways of the biliary tree.

Presently, the procedure for laparoscopic common bile duct exploration and stone removal is impaired by the surgeon's inability to visually monitor and simultaneously deploy a combination of instruments, as needed, to manipulate, destroy, or extract the stone. Multiple insertions of various tools and the choledochoscope through the laparoscopic ports are required to adequately explore and remove stones. Inadvertent damage to choledochoscopes commonly results from this repetitive process, which may also increase the possibility of complications due to prolonged operative time and increased potential for infection.

A surgeon may elect to use a lithotripter to destroy the stones in situ, which is a delicate process that requires very precise positioning of lithotripter-to-stone contact to avoid contact with (and perforation of) the common duct wall. Frequent reassessment of success, via choledochoscope, is required to judge the location and position of the stone within the bile duct. As a result of inadequate visualization of the process, this procedure is often tedious, stressful and frustrating for the surgeon. Often, after patient and diligent use of the various available instruments, the surgeon may fail to clear the common bile duct or intrahepatic bile duct of stones, as desired. As a result, surgeons frequently will not attempt the procedure using present laparoscopic common bile duct exploration techniques and prior art instruments. If a stone removal attempt is unsuccessful, then conversion to an open surgical procedure is typically required. Alternately, a subsequent endoscopic procedure (ERCP) may be required to attempt to clear the bile duct of stones, or the common bile duct is drained with a T-tube, and an attempt to dissolve stones with oral medications or infused solutions is made. A surrounding tract ideally forms around the T-tube within 6–8 weeks, whereby extraction of the stone from the bile duct is then again attempted by other radiologic or endoscopic surgical methods, in a much-delayed time frame.

With present stone retrieval procedures and surgical instrumentation, the combination of reduced visibility, restricted instrument sizes, need for multiple laparoscopic ports and/or tubular sheaths, and alternating insertions and retractions of instruments may present the practitioner with a complex and time-consuming procedure that still may fail to achieve the desired goal of stone removal. An improved system and innovative instrumentation are desired to provide surgeons with enhanced abilities to conduct laparoscopic common bile duct exploration and stone retrieval.

SUMMARY OF THE INVENTION

This invention has applicability in the performance of laparoscopic procedures related to exploration and the removal of physiologic calculi ("stones") from the common bile duct. Practitioners may benefit from the enhanced ability to concurrently insert instruments and a choledochoscope directly into a bile duct. This invention allows real-time video monitoring of the procedure, via choledochoscope, concurrently with the use of multiple instruments. An enhanced procedure as facilitated by this invention may expedite the extraction of stones while protecting the patient from prolonged operative procedures. In addition, an improved system of instruments are needed to minimize the occurrence of injury during use of lithotripter or laser and from injury resulting from hazardous migration of stone fragments that may lodge in the intrahepatic tree. These and related improvements may reduce patient trauma, minimize the necessity for conducting open surgical procedures, reduce costly damage to the choledochoscope and increase the success rate for laparoscopic common bile duct exploration and stone retrieval.

The present invention relates to a laparoscopic port adapter, related components and surgical devices. The laparoscopic port adapter of this invention may include a tubular laparoscopic port to provide a portal into the abdominal region, a tubular introducer sheath to be positioned concentrically through the laparoscopic port and substantially near the bile duct, and a multiple instrument guide. The introducer sheath may provide a through bore conduit for introducing at least one instrument guide into the bile duct. The instrument guide may have two or more through bore conduits and may include an occlusion balloon near an abdominal end of the instrument guide. Each multiple conduit instrument guide may include a straight, curved and/or flexible lower end and may provide an angled tip on the lower end to facilitate improved placement of the instrument guide within the bile duct.

In a preferred embodiment of the laparoscopic port adapter of this invention, a rigid introducer sheath may be inserted concentrically through a standard laparoscopic port. A flexible, multiple channel instrument guide having a curved lower end and angled tip may be inserted concentrically through the rigid introducer sheath to a depth adjacent to or within the common bile duct. The guide sheath and laparoscopic port may each include annular seals, connections and valves to facilitate and control insufflation of the peritoneal space within the abdominal cavity. The instrument guide may facilitate the concurrent introduction of the choledochoscope and other surgical instruments within and along bile duct passages for the purposed of exploration and stone removal, while also enhancing protection of the passages during the procedure.

A preferred embodiment of this invention may include a tubular, single conduit introducer sheath and a concentrically positioned tubular, multiple channel instrument guide having an angled, bent tip on the insertion end. The introducer sheath may be inserted concentrically through a laparoscopic port and through an abdominal cavity to a depth that is substantially just above the common bile duct. In a preferred embodiment, the instrument guide may have multiple conduits to allow the practitioner to simultaneously insert and guide various surgical instruments into the common bile duct while concurrently viewing the surgical process via a choledochoscope. This multiple tool guide may thus facilitate the surgeon's ability to visually monitor instrument use, manipulation and progress in the common bile duct on a continuous, real-time basis.

The advantages of the system as described herein may include a less extensive invasive procedure with shorter recovery time. The invention may typically eliminate the need for subsequent procedures of this nature to be performed. Also, other laparoscopic surgical procedures, such as gall bladder removal, may be concurrently possible. In addition, surgical practitioners may realize an improved rate of operational success through use of instrument devices, which provide means for real-time instrument manipulation, enhanced visual acuity, larger instrument size and selection options and reduced trauma to the patient.

It is an object of this invention to provide the practitioner with a more versatile and functional laparoscopic surgical system and to provide improved procedural techniques to enhance the surgeon's success rate by utilizing this invention. These improvements include simplifying the common bile duct exploration procedure, decreasing the time required for a procedure and reducing the number of invasive penetrations, thus lowering patient trauma and risk.

This invention may make use of common laparoscopic port sizes, typically between 5 mm and 12 mm. Previous to this invention, laparoscopic port instrument guides typically provided a single instrument channel, which was only sufficient for use and manipulation of a single instrument at a time. The introducer sheath of this invention preferably provides a single, relatively large conduit for introduction of a relatively large multiple channel instrument guide and associated components concentrically through the instrument guide.

The conduit channels in a preferred embodiment of the instrument guide of this invention may provide concurrent access for surgical instruments, irrigation and a choledochoscope. This port adapter and related introducer and guide devices may include a selection of conduit arrangements and/or size combinations as deemed appropriate by a practitioner and tailored to the procedure at hand. The instrument guide may be introduced through the introducer sheath after the introducer sheath is in place in the laparoscopic port as a separate introduction, or the instrument guide may be installed in the introducer sheath before the introducer sheath is introduced through the laparoscopic port.

An introducer sheath and instrument guide embodiment may be used for both a cholangiogram and for common bile duct exploration. The embodiment may offer advantages where multiple conduits and/or larger conduits may be desirable, including enhancing irrigation, concurrent real-time viewing, using multiple or larger instruments and improving instrument manipulation while concurrently diagnosing and observing the procedure continuously in real-time using a choledochoscope and video equipment. The multiple parallel channels allow instruments such as cholangiogram catheters, embolectomy catheters, balloon catheters, electro-hydraulic shock-wave lithotripter, laser, or a stone basket to be selectively inserted concurrently with each other and/or concurrently with a choledochoscope, thus permitting real-time procedural visualization. It will be apparent to those skilled in the art that the configuration and relative positions of the conduits with respect to each other and the general shape of the laparoscopic port adapter and related components is variable and may be tailored to procedural needs.

Deployment of instruments from the multiple conduit instrument guide of this invention is typically into the downstream region of the common bile duct. The instrument guide may alternatively include a "backdoor" conduit for simultaneous instrument access in the upstream direction of the common bile duct, substantially directionally oriented opposite from the instruments in the downstream portion of the duct. Access in the upstream portion of the duct may facilitate additional procedural options, such as positioning an occlusion balloon in the intrahepatic region for preventing hazardous migration of stone debris into the liver during irrigation and lithotripter stone destruction.

In many applications, it may be desirable to directionally steer the scope or instruments for entry into and guidance through the common bile duct, other anatomical passageways, a choledochotomy or other incision. In a preferred embodiment, the introducer sheath, preformed bent tip instrument guide and related components of this invention may enhance directional control or maneuverability of the instruments either within biliary and/or hepatic ducts, or external thereto without relying on external forceps manipulation through additional laparoscopic ports. A curved abdominal end of the instrument guide may be fabricated with a memorized bend such as may be elastically re-attained after concentrically passing the instrument guide through and exiting from a straight, rigid introducer sheath. The curved or bent lower end of the guide may enhance the spherical range of view as well as instrument manipulation. The maneuverability of the instrument guide tip and introduced instruments and scope may ultimately result in reduced trauma to the patient due to reduced need for additional laparoscopic ports for external manipulation of the scope or instruments using forceps or cables. This may also reduce procedural time requirements.

A feature of this invention is the ease of insertion of the instrument guide and instruments through the choledochotomy and into the bile duct. In contrast, the tip of prior art instrument guides typically remained external to the bile duct during the choledochotomy procedure, thereby requiring careful manipulation of the scope and instruments through the incision in the bile duct and severely limited manipulation inside the biliary tree while working against the obstructing closure force of the incision. This invention includes an angled tip and a curvature in the abdominal end of the instrument guide to facilitate instrument guide entry through the choledochotomy and into the bile duct such that instruments may be introduced into the bile duct parallel to the long axis of the duct. During instrument guide introduction into the duct, the choledochoscope and instruments may remain retracted and protected in the conduits in the instrument guide. After insertion of the instrument guide into the common bile duct, the practitioner may then selectively extend and retract the scope and various instruments as desired.

The bent abdominal end of the instrument guide may facilitate greater control of instrumentation manipulation and steering, reducing the necessity to relying upon additional laparoscopic ports and manipulation forceps. By having the choledochoscope positioned near the abdominal end of the instrument guide, or extended out of the instrument guide, the practitioner may continuously view instrument manipulation and perform the procedure while monitoring the procedure on video, in real time, from inside of the common bile duct and make diagnoses and procedural adjustments as desired. In addition, if so desired the practitioner may also utilize the instrument guide external to the common bile duct in the abdominal cavity, or in other anatomical passageways.

A preferred embodiment of the instrument guide may provide three conduits through the instrument guide. The first conduit may be used as a scope channel, providing passage for an insertion section of a choledochoscope. The choledochoscope may include an objective focusing lens lumen or conduit, a small instrument conduit and a light source. The instrument guide's second conduit may be used as an instrument channel or for irrigation/circulation. The third conduit may be used for instruments, such as a balloon catheter, stone basket or lithotripter. The instrument guide may also be compatible with presently available instrumentation and may provide advantages by allowing use of a thin, flexible scope without the present limitations of associated with tiny channels for irrigation or other tools. The invention may allow the surgical practitioner to control choledochoscope and multiple other various surgical tools through a single port site as opposed to inserting multiple ports and manipulation forceps in the abdominal cavity. A feature of the multiple instrument guide of this invention is that the guide may provide the option of using fewer but larger conduit channels.

This invention includes a centralizer component that may be used for scraping, trapping, grappling, crushing and removing calculi or stone debris. Numerous occlusion balloon options are available, permitting hydraulic isolation and/or insufflation of the common bile duct during the procedure. In addition, the entire procedure may be viewed continuously on video, in real time, likely improving the probability for a successful procedure. The depth of investigation along the passageways of the common bile duct may also be increased.

Another feature of this invention is an embodiment option that may include an occlusion balloon concentrically positioned along the instrument guide's lower end, substantially near the tip, such that after insertion of the tip of the guide into the common bile duct, the occlusion balloon may be inflated in the open incision or in the common bile duct, creating an annular seal therein as needed to hydraulically isolate the region of the common bile duct containing the stones. If desired, this seal may permit insufflation of the common bile duct facilitating enhanced viewing, diagnosis and operation inside of the duct and improving opportunities for removal or in-situ destruction of stones. This seal may also prevent undesirable migration of stone fragments into intrahepatic bile ducts or the liver and may facilitate enhanced control of circulation of fluids for removal of stone and calculus debris.

An additional feature of this invention is an embodiment option that may include a first occlusion balloon introduced into the bile duct through an instrument conduit and extended along the bile duct and beyond stones in the bile duct. The first occlusion balloon may then be inflated so as to position the stones between the first occlusion balloon and the tip of the guide. In addition, a second occlusion balloon may be provided on the curved abdominal end of the instrument guide, substantially near the tip of the guide. The second balloon may be inflated in the annulus between the instrument guide and the bile duct, thereby creating an annular seal therein to hydraulically isolate the region of the common bile duct between the two occlusion balloons, wherein the stones may be contained. If desired, this annular hydraulic seal may also permit insufflation of a portion of the common bile duct to facilitate enhanced viewing, diagnosis and operation inside of the duct, improving opportunities for removal or in-situ destruction of stones. This seal may also prevent undesirable migration of stone fragments into intrahepatic bile ducts or liver and may facilitate enhanced fluid control when irrigating or circulating fluids for removal of stone and stone debris.

In another embodiment, a separate or third occlusion balloon catheter may be separately or substantially simultaneously deployed in another region of the common bile duct to block undesirable migration of stones or debris into the intrahepatic duct. A dual-lumen (conduit) occlusion balloon having an inflation lumen and a fluid conducting lumen may be deployed to prevent stone or debris migration or envelop a stone. Such instrument may include multiple outlet ports substantially near the lower end of the fluid lumen that may be selectively opened or closed to direct the flow of irrigation fluid during the surgical procedure into specific positions within the bile duct which may thus facilitate enhanced fluid irrigation and circulation effectiveness within the bile duct during the surgical procedure.

Another instrument of this invention is a dual-lumen radial centralizer, which may be introduced as a standalone device or integrated into various known instruments, including a lithotripter, laser, choledochoscope or irrigation catheter. This device may be partially fabricated using memory wire or an elastically deformable material to provide a radial expansion of the centralizer segments to centralize surgical instruments within the common bile duct. This feature may be particularly desirable during the use of a fiber laser or electro-hydraulic shock-wave lithotripter, to prevent inadvertent damage to the bile duct wall and to facilitate precise laser or lithotripter to stone contact.

A grapple type centralizer device that may be manipulated by the practitioner may be included. The grapple type device may typically include three or four radially expandable segments that may be manipulated to envelope a stone. The stone may then be removed to the surface or crushed into smaller particulates.

Preferred and alternative embodiments of the laparoscopic port adapter of this invention may afford the practitioner numerous instrumental and procedural advantages in conducting procedures related to the biliary system, and in related laparoscopic procedures. This invention may offer numerous advantages over prior art, including reduced time and patient risk, and increased efficiency in performing common biliary, cystic duct and related exploration and operative procedures. It may also reduce the risk of damage to the choledochoscope by reducing the need to grasp and manipulate the scope with forceps. The required number of invasive port penetrations into the abdominal cavity may also be reduced, thus reducing patient trauma.

A preferred embodiment of the instrument guide including at least three conduits may afford a wide array of instrument sizes and functions to be introduced into the bile duct concurrently as desired by the practitioner. The multiple conduits in the instrument guide may facilitate the concurrent use of choledochoscope with lithotripter, laser, balloon catheter, papillatome or stone basket, along with fluid irrigation sufficient to distend and clear blood from the common bile duct during the process. The instrument guide system of this invention may allow clear, real-time visualization of the entire surgical process via the choledochoscope. This guide system may also provide more precise introduction of the choledochoscope into the choledochotomy, and may prevents or minimizes costly damage to the fragile choledochoscope, since manipulation with grasping forceps is not required. The multiple port guide system may thus allow real-time video viewing of the stone(s) within the common bile duct, concurrent with use of various tools to manipulate and remove or destroy the stone(s), thus clearing the common bile duct. As a result, the efficiency of laparoscopic common bile duct exploration and the stone removal procedure may be enhanced to the benefit of the patients. The iterative process of inserting, withdrawing and reinserting the choledochoscope and various other surgical instruments may be decreased.

The laparoscopic port adapter of this invention may improve the overall success of laparoscopic common bile duct and related procedures. As a result, the need for typically less desirable open surgical techniques and techniques relying upon multiple laparoscopic ports may be reduced. The time duration of the biliary and related hepatic laparoscopic procedures may also be reduced while increasing the efficiency and success of the procedures. These and further objects, features and advantages of the present invention will become apparent from the following detailed description, wherein reference is made to the figures in the accompanying drawings.

BRIEF DESCRIPTION OF THE DRAWINGS

FIG. 1 is a pictorial view, partially in cross-section of a laparoscopic port adapter assembly, penetrating an abdominal wall and with the instrument guide positioned within a bile duct.

FIG. 2 is a cross-section view of the instrument guide shown in FIG. 1, illustrating a plurality of three conduits in the instrument guide.

FIG. 3 illustrates a three channel instrument guide inserted into a bile duct, including three instruments inserted through the instrument guide and extending beyond the tip of the instrument guide, and including an inflated occlusion balloon encompassing the inserted tip of the instrument guide.

FIG. 7 illustrates an enlarged view of the irrigative balloon catheter shown in FIG. 6.

DETAILED DESCRIPTION

Figure 4:
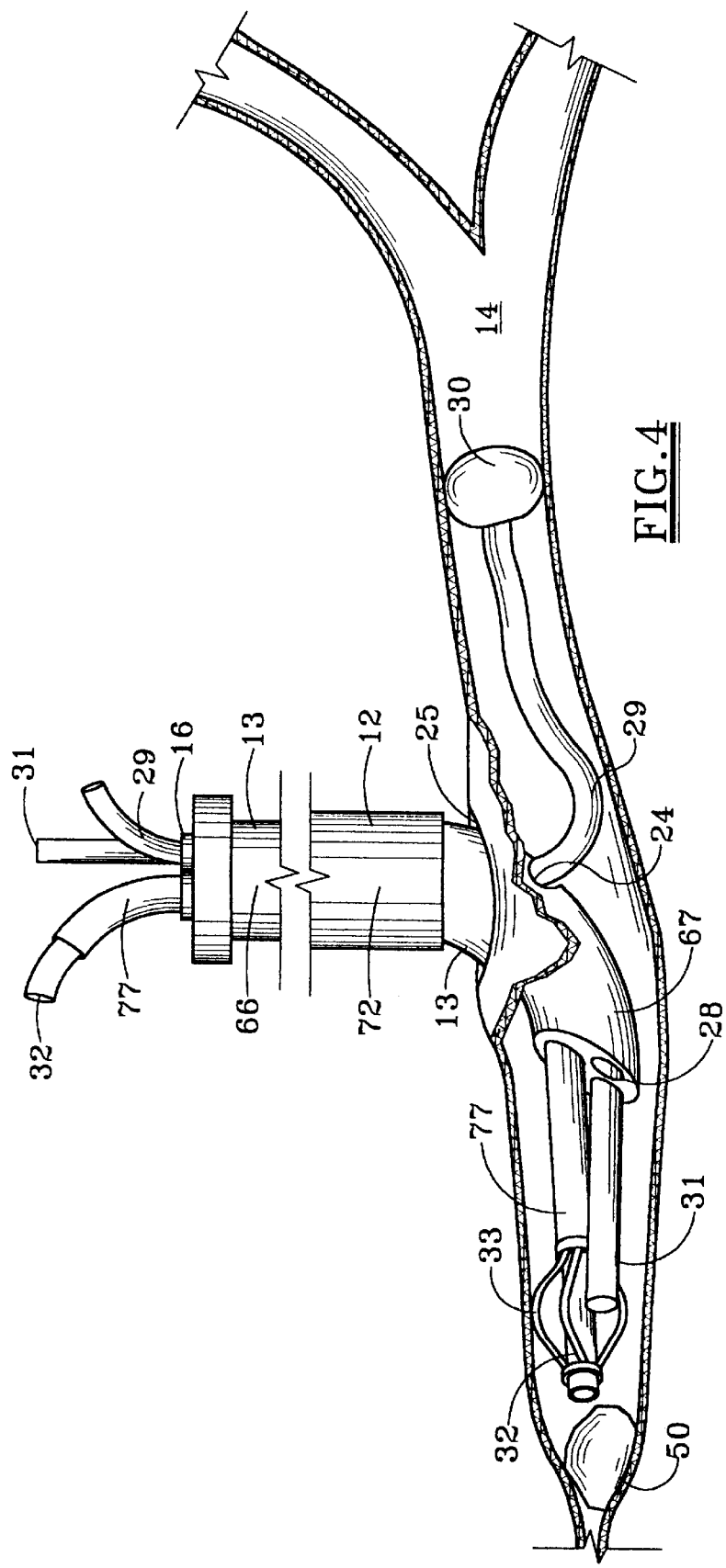
FIG. 4 illustrates a three channel instrument guide inserted into a bile duct, including three instruments inserted through the instrument guide, one of which instruments exiting the instrument guide through a "backdoor" opening to access the bile duct in an opposite direction from the orientation of the tip of the instrument guide.

FIG. 1 illustrates a suitable embodiment for a surgical laparoscopic instrument assembly for common bile duct exploration and stone removal according to the present invention. This invention facilitates conducting a bile duct procedure using a single laparoscopic port adapter assembly 10 without need for additional instrument manipulation ports. A "bile duct procedure" may be defined for purposes herein to include exploration, diagnosis, treatment, removal of physiologic calculi and associated procedures related to the common bile duct 14, other branches of the biliary tract, related hepatic tracts, Papillae of Vater, and related areas external to and within the biliary system.

A preferred embodiment of this invention, as illustrated in FIG. 1, may generally include a laparoscopic port adapter assembly 10 comprising a laparoscopic port 11, an introducer sheath 12 and an instrument guide 13, with the instrument guide 13 providing two or more through channels 26,27,28, a curved lower abdominal end 67 and an angled tip 74 to aid in insertion of the curved lower abdominal end 67 of the instrument guide 13 inside of a bile duct 14. The laparoscopic port 11 and introducer guide 12 may be manufactured from rigid or semi-rigid material, including metallic and/or non-metallic materials.

The laparoscopic port 11 may include one or more valves 15 to control insufflation of the abdominal cavity 23 by introduction of a pneumoperitoneum gas (not shown) through one or more of the valves 15. Pneumoperitoneum may be introduced into the abdominal cavity 23 between either the laparoscopic port 11 and the introducer sheath 12, or between the introducer sheath 12 and the instrument guide 13. Loss of pneumoperitoneum may be controlled with annular seals 75, 85 between concentrically positioned components of the laparoscopic adapter assembly 10. The laparoscopic port 11 may be positioned through in abdominal incision through the skin 18, subcutaneous layer 19, muscle 20 and peritoneum 21, forming a substantially pneumatic seal between an abdominal space 23 and the external atmosphere by means of a snug fit. Dedicated annular seals 16 may be included, such as O-rings or expandable membrane gaskets.

A curved end instrument guide 13 may provide three conduits or channels for selective fluid circulation and/or concurrent introduction of an array of instruments. Alternative embodiments of the instrument guide 13 may provide two or more conduits or instrument channels, including a conduit through which to inflate instrument guide occlusion balloon and/or channels leading exclusively to backdoor ports. The instrument guide 13 may be formed from a flexible material and may include a memorized or preformed curve or bend 67, which may be straightened for passage of the instrument guide 13 through the introducer sheath 12. Upon instrument guide 13 exit from an abdominal end of the introducer sheath 12, the pre-formed curve shape may be regained. An incision or choledochotomy 25 may be performed in the bile duct wall. The angled tip 74 of the instrument guide 13 may be maneuvered through the choledochotomy 25, thereby introducing the curved lower end 67 of the instrument guide 13 into the bile duct 14. The memorized curve of the instrument guide 13 may be such that the central axis of each conduit 26, 27, 28 in the instrument guide 13 substantially near the angled tip 74 of the instrument guide 13 is substantially parallel with a central axis through the bile duct 14. Instruments may thus be deployed from the instrument guide 13 substantially parallel with the bile duct 14. Various embodiments of angled tip 74 may include concave-curved geometry to facilitate instrument guide 13 tip-to-stone 50 contact, such as when engaging stone during removal of the stone from the choledochotomy.

Additional advantages of this invention may be realized through working within and deploying instruments directly in the bile duct 14, including being able to selectively isolate a first portion of the duct 14 from a second portion of the duct 14, thus preventing undesirable migration of particulate material into undesirable portions of the duct system. In addition, improved instrument control and manipulation may be achieved without the need for external manipulating forceps.

FIG. 2 is a cross-section view of a preferred embodiment of the invention, illustrating the instrument guide 13 concentrically positioned within an introducer sheath 12, which in turn is concentrically positioned within a laparoscopic port 11. In the preferred embodiment, channel 27 one of the three instrument channels may be relatively larger than the remaining two channels 26, 28 which may be of substantially same size.

FIGS. 1 and 3 illustrate an instrument guide 13 including an occlusion balloon 36 substantially adjacent the curved abdominal end 67 of the instrument guide 13 to provide a hydraulic seal in an annular area between the bile duct 14 and the instrument guide 13. The instrument guide occlusion balloon 36 may be substantially flush with the outer surface of the instrument guide 13 while deflated and during passage of the instrument guide 13 through the introducer sheath 12. When the instrument guide 13 is in proper position in the bile duct 14, a pneumatic pressure source may be activated from substantially adjacent the exterior end 66 of the instrument guide 13 and may be transmitted through a dedicated pressure channel 38 in the instrument guide 13, in order to inflate the balloon 36. Such pneumatic source may be provided by a hypodermic syringe 37, which may be connect to the dedicated pressure channel 38 by a tubing 35. The dedicated pressure channel may extend from the external end 66 of the instrument guide 13 to the occlusion balloon 36.

FIG. 3 also illustrates an array of instruments deployed through the relatively large conduit 27 and the two smaller conduits 26, 28. The larger conduit 27 may provide for introduction of a lithotripter 32, while the two smaller channels may provide for an irrigation catheter 34 and a choledochoscope 31. Additionally, FIG. 3 illustrates an inventive component of this invention, which includes a bow spring centralizer 33 that may be expanded to centralize a lithotripter 32 or substantially any other instrument within the bile duct 14. The centralizer 33 may be provided with any type of instrument that is inserted into the bile duct 14. Expansion of the centralizer 33 may be achieved through compression of the centralizer 33 by sliding movement of an outer sleeve 77 over the lithotripter 32. The opposing end of the centralizer 33 may be engaged with the lithotripter 32 such that upon compression, the spring segments of the centralizer 33 may radially expand. Although the lithotripter 32 is illustrated in FIG. 3, the lithotripter 32 or inner sleeve may be any instrument, which may be concentrically encased within an outer sleeve 77, including a choledochoscope 31, irrigative catheter 34, laser or any other instrument which may benefit from centralization within the bile duct 14. The sliding movement of the outer sleeve 77 relative to the lithotripter 32 may be actuated from above the external end of the guide tube 13. The integrated outer sleeve 77 and centralized inner instrument may be introduced into the bile duct 14 through one of the conduits in the instrument guide 13.

FIG. 3 also illustrates a backdoor port 24, which may be provided in an instrument guide 13. A backdoor port may communicate with one or more of the conduits 26, 27, 28 to provide improved bile duct access. The curved abdominal end 67 of the instrument guide 13 may be oriented for positioning the plurality of instruments in a first portion of the bile duct 14 and the backdoor channel 24 may be oriented to provide access to a second portion of the bile duct 14. Access to the bile duct 14 through a backdoor 24 may preferably be through one of the conduits which also provides access to the bile duct through the angled tip 74 of the instrument guide 13. To manipulate instruments either through or past the backdoor port 24, the instruments may be provided with a slight bend or angle of deflection such that directional steering may be facilitated by rotation of the instrument toward the desired conduit and opening. Memory wire may also be integrated into the instrument to provide a memorized deflection in the instrument. Alternatively, a plug or cap (not shown) may be provided in the instrument guide 13 which selectively restricts instrument entry through either the backdoor port 24 or the portion of conduit between the backdoor port 24 and the angled tip 74. Access to the backdoor ports may alternatively be provided through separate, designated conduits, which may undesirably result in a reduction in cross-sectional area availability for conduits leading to the angled tip end of the instrument guide 13.

The embodiment illustrated in FIG. 3 demonstrates the deployment of an instrument in each of three conduits in the instrument guide 13. A centralized lithotripter 32 may utilize a relatively large conduit 27, while a choledochoscope 31 and irrigation catheter 34 may be deployed in the remaining two instrument conduits 26, 28 in the instrument guide 13. Although the embodiment exhibits a backdoor port 24, no instrument is demonstrated accessing the backdoor port 24. An occlusion balloon 36 on the curved lower end 67 of the instrument guide 13 may be inflated to form a hydraulic seal in the bile duct 14 between the stone 50 or debris to be removed and the choledochotomy 25. Subsequent to the lithotripter 32 or laser destroying the stone 50, the lithotripter may be withdrawn from the instrument guide 13 to facilitate irrigation circulation of stone debris out of the bile duct 14 by circulating fluid into the bile duct 14 through the irrigation catheter 34 or through the vacant instrument conduit 27. The choledochoscope 31 may facilitate real-time viewing of the entire procedure within the bile duct. The inflated instrument guide balloon 36 may prevent migration of debris from within the bile duct 14 into other parts of the bile duct 14, or out of the choledochotomy 25 into the abdominal cavity.

FIG. 4 illustrates a three conduit instrument guide 13 positioned within a bile duct 14, demonstrating an instrument arrangement including a centralized lithotripter 32 and a choledochoscope 31 deployed from two conduits 27,26 in the instrument guide 13 and out the angled tip 74. The third conduit 28 may conduct an occlusion balloon catheter 29 and occlusion balloon 30 through a backdoor port 24. Such arrangement may facilitate in situ destruction of stones 50 while viewing with the scope. Subsequent to stone destruction, the centralized lithotripter 32 may be withdrawn out of the instrument guide 13 and an irrigation catheter may be inserted to wash stone debris out of the bile duct 14, through the choledochotomy 25 and into the abdominal cavity 23 where the debris may be suctioned or abandoned. Alternatively, a suction catheter or stone basket may be introduced to remove stone debris. The inflated balloon catheter 29, 30 may provide a hydraulic seal to prevent migration of stone debris into other branches of the bile duct 14.

Figure 5:
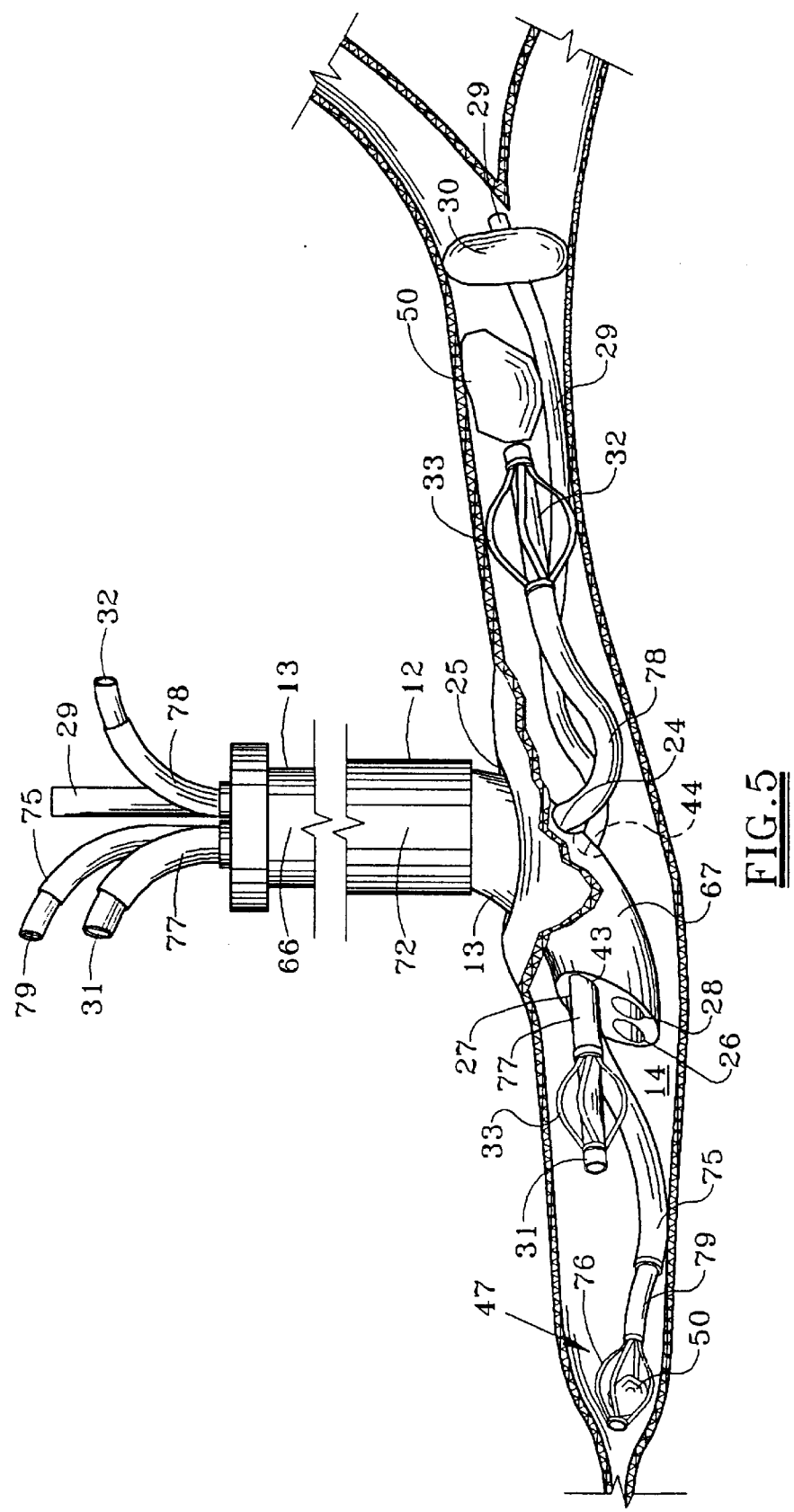
FIG. 5 illustrates a four channel instrument guide inserted into a bile duct, including four instruments inserted through the instrument guide, two of which instruments exit the instrument guide through "backdoor" openings to access the bile duct in an opposite direction from the orientation of the tip of the instrument guide where the remaining two instruments are deployed.

An alternative embodiment, as illustrated in FIG. 5, demonstrates an instrument guide 13 providing two backdoor ports 24,44 and including four instrument conduits 26, 27, 28, 43. A first of four instrument guide conduits 26 may conduct a centralized lithotripter 32 through a backdoor port 24, while a second conduit 28 may conduct a balloon catheter through a second backdoor 44. The balloon catheter 29, 30 may be manipulated past a stone 50 and inflated to provide an obstructing seal to prevent stone fragments from migrating into undesirable portions of the bile duct 14 after stone destruction using the lithotripter 32.

FIG. 5 also illustrates an alternative embodiment of the laparoscopic port adapter assembly 10, including a centralizer 33 adapted to grapple and/or manipulate stones 50. The grappling centralizer assembly 47 may be introduced through a third channel 27. The centralizer 33 may typically include three or four radially expandable segments 76 which, in addition to centralizing an instrument, may be manipulated to grapple, recover or crush a stone 50. This may be distinguished from prior art in that the centralizer 33 of this invention may include an instrument channel located concentrically through the centralizer 33 to permit introduction of an instrument or choledochoscope through the centralizer 33. The segments 76 may be constructed of memory wire or other flexible material that expands upon displacement from within an outer carrier sleeve 75 into the bile duct 14. The segments 76 may be extended from within the carrier sleeve 75 such that a stone 50 or other relatively large debris particle may be encompassed by the expanded segments 76. A centralized choledochoscope 31 may be introduced into the bile duct 14 through the fourth conduit 43 to aid in positioning the centralizer 33. The centralizer 33 may be expanded and contracted around a stone 50 by reciprocation of an inner actuation cable 79 which is affixed to the centralizer 33, within the outer carrier sleeve 75. A captured stone 50 may be retrieved from the bile duct 14 by removing the grappling centralizer assembly 47 from the bile duct 14 while carrying the stone 50. The centralizer 33 may also be used to crush the stone 50 into smaller fragments or debris for removal by other means. An irrigative fluid may be introduced into the bile duct 14 through the instrument channel in the inner actuation conduit 79.

In an alternative embodiment, a stone basket instrument (not shown) including a centralizer 33 may be introduced into the bile duct 14. The stone basket instrument may also be modified to include an irrigative catheter (not shown) integrated into the stone basket (not shown). The irrigative catheter/stone basket (not shown) may embody a conduit for the transmission of irrigating fluids at a rate sufficient to create a turbulent flow regime within the common bile duct 14. An occlusion balloon may be introduced into the bile duct 14 through a separate conduit in the instrument guide 13. The balloon may be positioned beyond the extended end of the irrigation catheter/stone basket. This procedure may be particularly useful in removing whole stones as well as debris remaining subsequent to laser or lithotripter use. The entire operation may be viewed continuously in real time video through concurrent use of a choledochoscope 32, introduced through an alternate conduit in the instrument guide 13.

Figure 6:
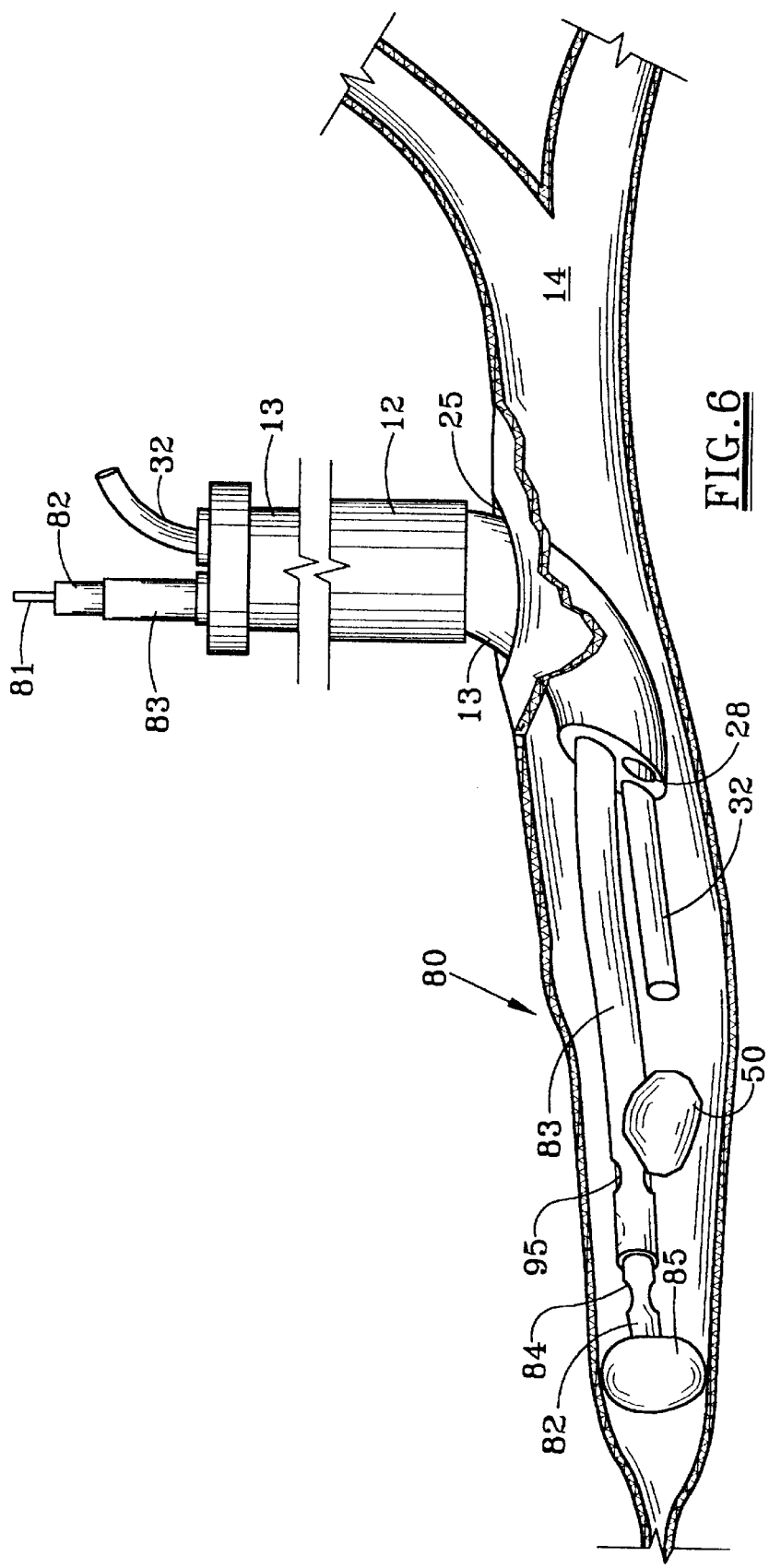
FIG. 6 illustrates an embodiment utilizing two instruments including an irrigative balloon catheter, a lithotripter.

FIGS. 6 and 7 illustrate an embodiment including an irrigative balloon catheter assembly 80. An irrigative balloon catheter assembly 80 may be introduced into the bile duct 14 through a conduit in the instrument guide 13. The irrigative balloon catheter assembly 80 may include a balloon 85 which may be inflated or deflated through a central tubing 81 which may be concentrically positioned within a first outer tubing 82. The first outer tubing 82 may be concentrically positioned within a second outer tubing 83. The first outer tubing 82 may include one or more ports 95 substantially near or along the balloon end of the irrigative balloon catheter assembly 80, to selectively direct fluid circulation along the bile duct 14 by aligning second outer ports 95 and first outer ports 84, 94. Irrigating fluid may be circulated in an irrigation annulus 88 between the outer surface of the central tubing 81 and the inner surface of the first outer tubing 82 and out of the annulus 88 through one or more ports 84, 94 and into the bile duct 14. Axial displacement of the first outer tubing 82 relative to the second outer tubing 83 may select the exact location along the irrigative balloon catheter assembly 80 at which irrigation fluid enters the bile duct 14, due to selective positioning of ports 84, 94 in the first outer tubing 82 relative to the position of the ports in the second outer tubing 83.

As illustrated in FIGS. 6 and 7, the irrigative balloon catheter assembly 80 may be positioned in the bile duct 14, through one of the conduit channels in the instrument guide 13, such that a stone 50 is located between the balloon 85 and the choledochotomy 25. A laser or lithotripter 32 may be introduced through a second conduit in the instrument guide 13 and positioned adjacent the stone 50 to destroy the stone, in situ. A choledochoscope 31 may be introduced into the bile duct 14 through a third conduit in the instrument guide 13 and positioned to observe the procedure in real time. The balloon 85 may be pneumatically inflated through central tubing 81. As the lithotripter 32 destroys the stone 50 in situ, irrigative fluid may circulate the debris from the bile duct 14 and out of the field of view of the camera and into the abdominal cavity 23 for suction removal or otherwise. The inflated balloon 85 may prevent migration of debris into other portions of the bile duct 14. Alternatively, after stone 50 destruction, the lithotripter 32 may be removed from the instrument guide 13 and debris circulated out of the bile duct 14 by using a vacant conduit in the instrument guide 13. An instrument guide occlusion balloon 36 may be included to prevent fluid loss or stone debris within the bile duct 14 from entering either the abdominal cavity 23 or other portions of the bile duct 14.

In an alternative embodiment, an instrument guide 13 may also provide for the concentric passage of a second instrument guide (cannula) through the instrument guide 13. The second instrument guide may also concentrically contain an instrument or surgical device, such that the second instrument guide may control and enhance the extension of the instruments or devices beyond the abdominal end of the first instrument guide 13. The instrument may otherwise be too flimsy to sufficiently extend, difficult to control, or may require additional support or protection than would otherwise be available without such cannula to transport the instrument.

The expanded procedural capabilities of this laparoscopic port adapter assembly may facilitate the introduction of instruments into the bile duct 14 which may provide enhanced means for stone 50 and debris removal which may not have been previously feasible. This invention may facilitate the introduction of wash tools which may provide directionally oriented fluid streams, relatively high volume turbulent-flow wash tools, instruments for the removal of stones which may be impacted in a wall of the bile duct 14, instruments which may expand the bile duct 14, or instruments which may scrape or otherwise clean the walls of the duct 14. Centralizers may be expanded in the bile duct 14 and used to grapple or scrape stone debris from the bile duct wall, swab stones from within the bile duct 14 and/or occlude the bile duct 14 to prevent migration of stones 50. A papillatome (not shown) may be inserted through a channel in the instrument guide 13 to cut and enlarge and ampullae of vater (not shown). A biopsy forceps (not shown) may be inserted through the instrument guide 13 to biopsy the bile duct wall or ampullae of vater. Numerous variations of the instruments, carriers, instrument guides, centralizer, introducer sheath and laparoscopic port described herein will be conceivable to those skilled in the art.

It may be appreciated that various changes to the methods or steps herein, as well as in the details of the illustrations, methods and systems may be made within the scope of the attached claims without departing from the spirit of the invention. While preferred embodiments of the present invention have been described and illustrated in detail, it is apparent that still further modifications and adaptations of the preferred and alternative embodiments will occur to those skilled in the art. However, it is to be expressly understood that such modifications and adaptations are within the spirit and scope of the present invention, which is set forth in the following claims.

What is claimed is:

1. A surgical laparoscopic port adapter assembly for conducting a bile duct procedure, comprising:

a laparoscopic port having an external end extending above an external surface of the abdominal wall and an abdominal end extending below an internal surface of the abdominal wall into an abdominal cavity, the laparoscopic port including an internal through bore extending between the external end and the abdominal end to provide a conduit into the abdominal cavity;

an instrument guide received within the laparoscopic port internal through bore and having an instrument guide external end and an instrument guide abdominal end, the instrument guide external end extending above the external surface of the abdominal wall and the instrument guide abdominal end extending below the laparoscopic port abdominal end and into the bile duct, the instrument guide further including two or more through channels, each through channel conveying and deploying one of the plurality of instruments; and the instrument guide including a curved portion in the abdominal end of the instrument guide and an angled tip on the abdominal end of the instrument guide for ease of inserting the instrument guide into a choledochotomy in the bile duct.

2. The surgical laparoscopic port adapter assembly as defined in claim 1, further comprising:

an introducer sheath received within the laparoscopic port internal through bore and having an introducer external end and an introducer abdominal end, the introducer external end extending above the external end of the laparoscopic port and the introducer abdominal end extending below the abdominal end of the laparoscopic port, the introducer sheath having an internal through bore extending from the introducer external end to the introducer abdominal end, the introducer sheath providing a conduit for introduction of the instrument guide through the introducer sheath and into the bile duct.

3. The surgical laparoscopic port adapter assembly as defined in claim 1, further comprising:

one or more seals for sealing between the laparoscopic port and the instrument guide; and one or more valves to control insufflation of the abdominal cavity and to prevent loss of pneumoperitoneum.

4. The surgical laparoscopic port adapter assembly as defined in claim 1, wherein at least one of the plurality of instruments is selected from a group consisting of:

a choledochoscope for real-time viewing the bile duct procedure;

an occlusion balloon catheter including an occlusion balloon to fluidly isolate a first portion of the bile duct from a second portion of the bile duct;

a stone basket to facilitate removal of physiologic calculi;

an electro-hydraulic lithotripter to destroy physiologic calculi in suit;

a laser to destroy physiologic calculi in situ;

a papillatome to cut and enlarge the ampullae of vater; and an irrigative catheter to selectively irrigate a portion of the bile duct.

5. The surgical laparoscopic port adapter assembly as defined in claim 1, wherein one of the plurality of instruments is an irrigative balloon catheter to selectively isolate a first portion of the bile duct from a second portion of the bile duct while selectively irrigating a portion of the bile duct.

6. The surgical laparoscopic port adapter assembly as defined in claim 1, wherein one of the plurality of instruments is a centralizer having a plurality of selectively radially expandable and collapsible segments to concentrically centralize one or more of the plurality of instruments inside of the bile duct.

7. The surgical laparoscopic port adapter assembly as defined in claim 1, wherein the instrument guide includes at least three through channels.

8. The surgical laparoscopic port adapter assembly as defined in claim 1, wherein the curved portion is oriented for positioning the plurality of instruments in a first portion of the bile duct an the instrument guide includes a backdoor channel oriented to position an instrument in a second portion of the bile duct.

9. The surgical laparoscopic port adapter assembly as defined in claim 1, further comprising:

instrument guide occlusion balloon adjacent the abdominal end of the instrument guide to hydraulically seal in an annular area between the bile duct and the instrument guide.

10. The surgical laparoscopic port adapter assembly as defined in claim 1, wherein the angled tip of the instrument guide has a concave geometry to facilitate receiving a stone during removal of the stone.

11. A surgical method of performing a bile duct procedure using a plurality of instruments, comprising:

inserting an abdominal end of a laparoscopic port through an abdominal wall and into an abdominal cavity to provide a conduit into an abdominal cavity;

inserting an instrument guide through the laparoscopic port until an abdominal end of the instrument guide is within the bile duct, the instrument guide having two or more through channels;

inserting each of two or more instruments into a respective one of the two or more through channels of the instrument guide, wherein one of the two or more instruments is a choledochoscope for real-time viewing the bile duct; and extending each of the two or more instruments beyond the abdominal end of the instrument guide and into the bile duct to perform the bile duct procedure.

12. The surgical method of performing a bile duct procedure as defined in claim 11, further comprising:

inserting an abdominal end of an introducer sheath through the laparoscopic port; and extending the abdominal end of the introducer sheath below the abdominal end of the laparoscopic port to provide a conduit for introduction of the instrument guide through the introducer sheath and into the bile duct.

13. The surgical method of performing a bile duct procedure as defined in claim 11, further comprising:

introducing pneumoperitoneum through the laparoscopic port and into the abdominal cavity to insufflate the abdominal cavity; and controlling insufflation of the abdominal cavity by the pneumoperitoneum.

14. The surgical method of performing a bile duct procedure as defined in claim 11, further comprising:

inserting an occlusion balloon catheter through one of the two or more through channels of the instrument guide, the occlusion balloon catheter being one of the two or more instruments; and inflating the occlusion balloon catheter to fluidly isolate a first portion of the bile duct from a second portion of the bile duct.

15. The surgical method of performing a bile duct procedure as defined in claim 11, further comprising:

inserting a stone basket through one of the two or more through channels of the instrument guide, the stone basket being one of the two or more instruments; and removing physiologic calculi with the stone basket.

16. The surgical method of performing a bile duct procedure as defined in claim 11, further comprising:

inserting an electro-hydraulic lithotripter through one of the two or more through channels of the instrument guide, the electro-hydraulic lithotripter being one of the two or more instruments; and destroying physiologic calculi in situ with the electro-hydraulic lithotripter.

17. The surgical method of performing a bile duct procedure as defined in claim 11, further comprising:

inserting an irrigative catheter through one of the two or more through channels of the instrument guide, the irrigative catheter being one of the two or more instruments; and selectively irrigating a portion of the bile duct using an irrigant fluid and the irrigative catheter to remove stones and debris.

18. The surgical method of performing a bile duct procedure as defined in claim 11, further comprising:

inserting an irrigative balloon catheter through one of the two or more through channels of the instrument guide, the irrigative balloon catheter being one of the two or more instruments;

inflating an irrigative balloon catheter and selectively isolating a first portion of the bile duct from a second portion of the bile duct; and selectively irrigating a first portion of the bile duct using an irrigant fluid to remove stones and debris.

19. The surgical method of performing a bile duct procedure as defined in claim 11, further comprising:

inserting a biopsy forceps through one of the two or more through channels of the instrument guide, the biopsy forceps being one of the two or more of the plurality of instruments; and selectively removing a biopsy sample with the biopsy forceps.

20. The surgical method of performing a bile duct procedure as defined in claim 11, further comprising:
  inserting one of the two or more instruments through one of the two or more through channels of the instrument guide; and
  enlarging an opening in the ampullae of vater using the one of the two or more instruments to facilitate passage of stones.

21. The surgical method of performing a bile duct procedure as defined in claim 11, further comprising:
  providing at least three through channels in the instrument guide for introducing a plurality of instruments through the instrument guide and into the bile duct.

22. The surgical method of performing a bile duct procedure as defined in claim 11, further comprising:
  inserting an instrument into the bile duct through a backdoor channel in the instrument guide, wherein a curved portion of the instrument guide is oriented for positioning of the plurality of instruments in a first portion of the bile duct and the instrument guide includes the backdoor channel oriented to position an instrument in a second portion of the bile duct opposite the first portion with respect to the curved portion of the instrument guide.

23. The surgical method of performing a bile duct procedure as defined in claim 11, further comprising:
  hydraulically sealing an annular area inside of the bile duct with an instrument guide occlusion balloon between a choledochotomy in the bile duct and the tip of the instrument guide with the instrument guide occlusion balloon substantially adjacent the abdominal end of the instrument guide.

24. The surgical method of performing a bile duct procedure as defined in claim 11, further comprising:
  inserting a laser through one of the two or more through channels of the instrument guide, the laser being one of the two or more instruments; and
  destroying physiologic calculi in situ with the laser.

25. A surgical laparoscopic port adapter assembly for conducting a bile duct procedure, comprising:
  a laparoscopic port having an external end extending above an external surface of the abdominal wall and an abdominal end extending below an internal surface of the abdominal wall into an abdominal cavity, the laparoscopic port including an internal through bore extending between the external end and the abdominal end to provide a conduit into the abdominal cavity;
  an instrument guide received within the laparo,copic port internal through bore and having an instrument guide external end and an instrument guide abdominal end, the instrument guide external end extending above the external surface of the abdominal wall and the instrument guide abdominal end extending below the laparoscopic port abdominal end and into the bile duct, the instrument guide further including two or more through channels, each through channel conveying and deploying one of a plurality of instruments; and
  an introducer sheath received within the laparoscopic port internal through bore and having an introducer external end and an introducer abdominal end, the introducer external end extending above the external end of the laparoscopic port and the introducer abdominal end extending below the abdominal end of the laparoscopic port, the introducer sheath having an internal through bore extending from the introducer external end to the introducer abdominal end, the introducer sheath providing a conduit for introduction of the instrument guide through the introducer sheath and into the bile duct.

26. The surgical laparoscopic port adapter assembly as defined in claim 25, further comprising:
  one or more seals for sealing between the laparoscopic port and the instrument guide; and
  one or more valves to control insufflation of the abdominal cavity to prevent loss of pneumoperitoneum.

27. The surgical laparoscopic port adapter assembly as defined in claim 25, wherein one of the plurality of instruments is an irrigative balloon catheter to selectively isolate a first portion of the bile duct from a second portion of the bile duct while selectively irrigating a portion of the bile duct.

28. The surgical laparoscopic port adapter assembly as defined in claim 25, wherein one of the plurality of instruments is a centralizer having a plurality of selectively radially expandable and collapsible segments to concentrically centralize one or more of the plurality of instruments inside of the bile duct.

29. The surgical laparoscopic port adapter assembly as defined in claim 25, wherein the instrument guide includes at least three through channels.

30. The surgical laparoscopic port adapter assembly as defined in claim 25, wherein the instrument guide includes a curved portion in an abdominal end of the instrument guide and an angled tip on the abdominal end of the instrument guide for ease of inserting the instrument guide into a choledochotomy in the bile duct, and the curved portion is oriented for positioning the plurality of instruments in a first portion of the bile duct and the instrument guide includes a backdoor channel oriented to position an instrument in an second portion of the bile duct.

31. The surgical laparoscopic port adapter assembly as defined in claim 25, wherein one of the plurality of instruments is a choledochoscope for real-time viewing of the bile duct procedure.

32. The surgical laparoscopic port adapter assembly as defined in claim 25, wherein at least one of the plurality of instruments is selected from a group consisting of:
  a choledochoscope for real-time viewing the bile duct procedure;
  an occlusion balloon catheter including an occlusion balloon to fluidly isolate a first portion of the bile duct from a second portion of the bile duct;
  a stone basket to facilitate removal of physiologic calculi;
  an electro-hydraulic lithotripter to destroy physiologic calculi in suit;
  a laser to destroy physiologic calculi in situ;
  a papillatome to cut and enlarge the ampullae of vater; and
  an irrigative catheter to selectively irrigate a portion of the bile duct.

33. The surgical laparoscopic port adapter assembly as defined in claim 25, wherein the instrument guide includes an angled tip on an abdominal end of the instrument guide for ease of inserting the instrument guide into a choledochotomy in the bile duct, and the angled tip has a concave geometry to facilitate receiving a stone during removal of the stone.

* * * * *